US011103432B2

(12) United States Patent
Redoules et al.

(10) Patent No.: US 11,103,432 B2
(45) Date of Patent: Aug. 31, 2021

(54) USE OF 1,3 DIGLYCERIDE IN A TOPICAL COMPOSITION FOR COUNTERING THE WEAKENING OF THE SKIN BARRIER

(71) Applicant: PIERRE FABRE DERMO-COSMETIQUE, Boulogne-Billancourt (FR)

(72) Inventors: Daniel Redoules, Toulouse (FR); Gwendal Josse, Toulouse (FR)

(73) Assignee: PIERRE FABRE DERMO-COSMETIQUE, Boulögne-Billancourt (FR)

(*) Notice: Subject to any disclaimer, the term of this patent is extended or adjusted under 35 U.S.C. 154(b) by 0 days.

(21) Appl. No.: 16/843,587

(22) Filed: Apr. 8, 2020

(65) Prior Publication Data

US 2020/0246236 A1 Aug. 6, 2020

Related U.S. Application Data (63) Continuation of application No. 15/778,343, filed as application No. PCT/EP2016/080295 on Dec. 8, 2016, now abandoned.

(30) Foreign Application Priority Data

Dec. 8, 2015 (FR) ...................................... 1561994

(51) Int. Cl.
  *A61K 8/37* (2006.01)
  *A61Q 17/00* (2006.01)
  *A61Q 19/00* (2006.01)
  *A61K 8/06* (2006.01)

(52) U.S. Cl.
  CPC .................. *A61K 8/37* (2013.01); *A61K 8/06* (2013.01); *A61Q 17/00* (2013.01); *A61Q 19/00* (2013.01); *A61Q 19/005* (2013.01)

(58) Field of Classification Search
  CPC .......... A61K 8/37; A61Q 19/00; A61Q 17/00; A61Q 19/005; A61P 17/00
  See application file for complete search history.

(56) References Cited

U.S. PATENT DOCUMENTS

| 4,551,332 A | * | 11/1985 | Stillman | ............... | A61K 36/185 |
| | | | | | 424/401 |
| 4,957,740 A | * | 9/1990 | Wilder | ..................... | A61K 8/66 |
| | | | | | 424/94.1 |

FOREIGN PATENT DOCUMENTS

| DE | 4430851 C1 | 9/1995 |
| EP | 1216690 A2 | 6/2002 |
| GB | 2318364 A | 4/1998 |
| JP | 52-61240 A | 5/1977 |
| JP | 2-115117 A | 4/1990 |
| KR | 10-1425966 B1 | 8/2014 |
| WO | WO03/014073 A1 | 2/2003 |
| WO | WO 2004/084646 A2 | 10/2004 |
| WO | WO-2004084646 A2 * | 10/2004 | ............. A61Q 19/08 |

OTHER PUBLICATIONS

MSDS "Glyceryl 1,3-distearate" (http://datasheets.scbt.com/sc-215081.pdf) Jun. 7, 2011, pp. 1-7 (Year: 2011).*
Sigma (https://www.sigmaaldrich.com/catalog/substance/glyceryldistearate62502132383711?lang=en&region=US) accessed Oct. 8, 2019, p. 1 (Year: 2019).*
Berthaud et al., "Correlation between the Properties of the Lipid Matrix and the Degrees of Integrity and Cohesion in Healthy Human Stratum corneum," Experimental Dermatology, vol. 20, No. 3, 2010 (Mar. 2011), pp. 255-262.
Boncheva et al., "Molecular Organization of the Lipid Matrix in Intact Stratum corneum Using ATR-FTIR Spectroscopy," Biochimica et Biophysica Acta, vol. 1778, No. 5, 2008 (Available online Feb. 11, 2008), pp. 1344-1355.
Cho et al., "Infrared Plus Visibile Light and Heat from Natural Sunlight Participate in the Expression of MMPs and Type I Procollagen as Well as Infiltration of Inflammatory Cell in Human Skin in vivo," Journal of Dermatological Science, vol. 50, 2008, pp. 123-133.
Coderch et al., "Ceramides and Skin Function," Am J Clin Dermatol, vol. 4, No. 2, 2003, pp. 107-129.
Damien et al., "The Extent of Orthorhombic Lipid Phases in the Stratum Corneum Determines the Barrier Efficiency of Human Skin In Vivo," Journal of Investigative Dermatology, vol. 130, No. 2, 2010 (Published online Sep. 3, 2009), pp. 611-614.
Groen et al., "Is an Orthorhombic Lateral Packing and a Proper Lamellar Organization Important for the Skin Barrier Function?" Biochimica et Biophysica Acta, vol. 1808, No. 6, 2011 (Available online Oct. 28, 2010), pp. 1529-1537.
Liu et al., "Fast Synthesis of 1,3-DAG by Lecitase® Ultra-catalyzed Esterification in Solvent-free System," Eur. J. Lipid Sci. Technol., vol. 113, 2011, pp. 973-979.
May et al., "Solution Thermodynamics of Some Slightly Soluble Hydrocarbons in Water," Journal of Chemical and Engineering Data, vol. 28, No. 2, Apr. 1983, pp. 197-200 (5 pages total).
Mintel Group, Ltd, "L'Oreal Skin Perfect Age 30+," L'Oreal, India, GNPD—Anti-Ageing Whitening Facial Foam, Oct. 2015, 2 pages.
Mintel Group, Ltd, "Trind Perfect System," Trind Cosmetics, Netherlands, GNPD Hand Repair Product Details, Mar. 2015, 1 page.

(Continued)

Primary Examiner — Andrew S Rosenthal
(74) Attorney, Agent, or Firm — Birch, Stewart, Kolasch & Birch, LLP (57) ABSTRACT

This invention relates to a topical, cosmetic or dermatological composition, comprising a 1,3 diglyceride having the general formula (I), in which the radicals R1 and R2 represent, independently of one another, a C13 to C40 saturated and linear alkyl radical, and at least one cosmetic or dermatological excipient for a topical application on the skin. This invention also relates to such a composition, or a 1,3 diglyceride having the formula (I), for its use in protecting the skin, in countering the weakening of the skin barrier and in preventing or reducing the penetration of exogenous molecules into the skin following a weakening of the skin barrier.

10 Claims, 4 Drawing Sheets

(56) References Cited

OTHER PUBLICATIONS

MSDS, "Glyceryl 1,3-distearate", (http://datasheets.scbt.com/sc-215081.pdf), Jun. 7, 2011, 7 pages.
Scalia et al., "Encapsulation of the UV Filters Ethylhexyl Methoxycinnamate and Butyl Methoxydibenzoylmethane in Lipid Microparticles: Effect on in vivo Human Skin Permeation," Skin Pharmacol Physiol, vol. 24, No. 4, 2011 (Published online Feb. 17, 2011), pp. 182-189.
Seo et al., "Thermal Aging: A New Concept of Skin Aging," Journal of Dermatological Science Supplement, vol. 2, No. 1, 2006, pp. S13-S22.
Sigma-Aldrich, "Glyceryl distearate", (https://www.sigmaaldrich.com/catalog/substance/glyceryldistearate62502132383711?lang=U accessed Oct. 8, 2019, 1 page.
Singer Instruments, "High-throughput Screening Assays", (https://www.singerinstruments.com/resource/what-is-high-throughput-screening/) Mar. 24, 2015, pp. 1-9.

Written Opinion of the International Searching Authority and International Search Report (forms PCT/ISA/237 and PCT/ISA/210), dated Feb. 7, 2017, for International Application No. PCT/EP2016/080295.
"Amended Final Report on the Safety Assessment of Glyceryl Dilaurate, Glyceryl Diarachidate, Glyceryl Dibehenate, Glyceryl Dierucate, Glyceryl Dihydroxystearate, Glyceryl Diisopalmitate, Glyceryl Diisostearate, Glyceryl Dilinoleate, Glyceryl Dimyristate, Glyceryl Dioleate, Glyceryl Diri ci noleate. Glyceryl Dipalmitate, Glyceryl Dipalmitoleate, Glyceryl Distearate, Glyceryl Palmitate Lactate, Glyercol Stearate Citrate, Glyceryl Stearate Lactate, and Glyceryl Stearate Succinate," InternationalJournal of Toxicology (2007), vol. 26, No. 3, pp. 1-30.
Zhong et al., "Solvent-free enzymatic synthesis of 1,3-Diacylglycerols by direct esterification: of glycerol with, saturated fatty acids," Lipids in Health and Disease (2013), vol. 12, No. 65, pp. 1-7.

* cited by examiner

USE OF 1,3 DIGLYCERIDE IN A TOPICAL COMPOSITION FOR COUNTERING THE WEAKENING OF THE SKIN BARRIER

CROSS-REFERENCE TO RELATED APPLICATIONS

This application is a Continuation of copending application Ser. No. 15/778,343, filed on May 23, 2018, which is the National Phase under 35 U.S.C. § 371 of International Application No. PCT/EP2016/080295, filed on Dec. 8, 2016, which claims the benefit under 35 U.S.C. § 119(a) to Patent Application No. 1561994, filed in France on Dec. 8, 2015, all of which are hereby expressly incorporated by reference into the present application.

This invention relates to a cosmetic or dermatological composition, intended to be administered topically, comprising at least one 1,3 diglyceride defined hereinafter, as well as its use for improving the resistance of the stratum corneum, in particular to environmental factors such as the cold or heat, and as such preserve its properties as a skin barrier.

One of the main functions of the skin is to form a physical barrier that, in addition to its protective role with respect to the environment by preventing the penetration of aggressive microbial or chemical elements, must provide the maintaining of the physiological medium of the organism by limiting water loss, thanks to a relative hydrophobicity. Although there is still controversy concerning the various paths of transcutaneous passage, it is admitted for the most part that the penetration via the intercorneocytory spaces also serves as an element for regulating the permeability of the skin [1]. The substantial number of adsorption-desorption sequences associated with the diffusion of molecules through lamellar layers of the corneum determines the effectiveness of the skin barrier. The diffraction of X-rays, used for the characterisation of the latter, reveals the presence of two lamellar phases with repetition distances of 6 and 13 nm which are mostly located in crystalline lateral phases (orthorhombic lateral arrangement) [2, 3, 4]. Indeed, at physiological temperature, the aliphatic long chains of ceramides and of fatty acids form with the cholesterol and the esters thereof gelled states that are impermeable to the transepidermal flow of water.

In subjects whose skin barrier is intact, the transepidermal flow of water, (also called TransEpidermal Water Loss—TEWL) is about 5 mg/cm$^2$ [5] but it can reach higher values in case of external aggressions due to various environmental factors such as the cold or heat. In this respect, it has been shown that a simple exposure for an average of 3 hours in conditions of average outdoor sunshine (outside temperature of 26.6° C.) was sufficient to induce an increase of 4.7° C. in the skin temperature (initially at 31.7° C.) [6] and that the latter can exceed 40° C. after only 20 minutes of exposure to the sun at solar noon in the summer [7]. Such an elevation in the skin temperature then causes a fluidification of the lipids of the intercorneocytory spaces, which change to a state of the liquid crystal type giving rise to a substantial increase in transepidermal water loss [4].

As such, the altering/weakening of the skin barrier allows for an increased penetration of exogenous substances (polluting agents, irritant agents or allergenic substances (also called allergens)), preferably lipophilic exogenous substances, which can sometimes cause irritations or allergic reactions or oxidative stress.

In addition to being allergenic, certain volatile organic polluting agents, such as benzo[a]pyrene released from exhaust gases, are also considered to be carcinogenic (carcinogen of Group 1).

Diglycerides are known in literature and have biological, cosmetics and/or therapeutic activities. It is known in document KR 2013058299 the use of a composition comprising 1,3-diolein or 1,3-dilinoleoyl-rac-glycerol for preventing or treating hyperpigmentation. Likewise, preparations with a fatty acid derivative base among which diglycerides have been able to be claimed for countering the ageing of the skin (WO 03/014073 A1), as an emollient (JP02115117 A) or used in sticks for caring for lips (JP52061240A). Certain diglycerides are used at a low concentration (<1% by weight) as a texturising agent in cosmetic compositions. However, to date, no document describes or suggests that 1,3 diglycerides can have interesting properties in order to overcome the weakening in the skin barrier function, in particular under the effect of environmental factors (cold, heat).

This invention as such aims to overcome the disadvantages of prior art by proposing active stabilisers of the intercorneocytory spaces and their use in cosmetic or dermatological compositions so as to counter the weakening of the skin barrier, in particular under the effect of environmental factors. The obtaining of greater stability of the intercorneocytory spaces will as such make it possible to open new perspectives in the fields of cosmetics and dermatology for skincare and/or make-up products for the skin, including facial skin, body skin and scalp. Such active agents can be used in topical cosmetic or dermatological compositions for protecting the skin, including facial skin, body skin and scalp, in particular against some deleterious effects (such as allergy, irritation, etc.) due to the penetration into the skin of exogenous substances, such a cutaneous penetration being increased under the effect of environmental factors, such as heat.

Thus it has been noticed, and this surprisingly and in a completely unexpectedly manner, that the use of a 1,3 diglyceride having the general formula (I):

in which the radicals $R_1$ and $R_2$ represent, independently of one another, a C13 to C40 saturated and linear alkyl radical, in a cosmetic or dermatological composition made it possible, after being applied topically, to limit the weakening of the skin barrier that can be due to environmental factors. The inventors have in particular revealed that these 1,3 diglycerides, when they are applied on the skin, stabilise the change in state of the lipids present in the intercorneocytory spaces; this change in state is observed in particular under the effect of the temperature.

In order to evaluate the change in the organisation of the lipid phases of the stratum corneum, the inventors used infrared spectroscopy (ATR-FTIR: Attenuated total reflectance—Fourier transform infrared Spectroscopy) to analyse the variation, under the effect of the temperature, of the fundamental vibration bands of the $vCH_2$ aliphatic chains of these lipids. More particularly, the position of the absorption band, corresponding to the stretching of the $CH_2$, is located around wave number 2848 cm$^{-1}$. By way of example, an increase in the temperature of the surface of the skin causes a displacement of this bands to the higher wave numbers. This displacement reveals the fact that the lipids in the stratum corneum adopt, under the effect of the heat, a less-ordered conformation accompanied by an increase in the fluidity of the hydrocarbon chains that fill the intercorneocytory spaces (see example 1).

In the framework of this invention, it has also been demonstrated that, on the one hand, the stabilising power of the 1,3 diglycerides, on the heated lipid phase, increases with the length of the esterified chains (see example 2) and on the other hand, that the 1,3 diglycerides have a stabilising effect of the heated lipid phase that is much greater than that observed with diglycerides 1,2 (see example 3). It is however not excluded in the framework of this invention to use a 1,3 diglyceride that would be in a mixture with small quantities of 1,2 diglycerides often present due to industrial production conditions.

In addition, a study in vivo on healthy volunteers made it possible to show that applying glyceryl 1,3 distearate makes it possible to stabilise the organisation of the intercorneocytory lipids of the skin heated between 30 and 45° C. This beneficial effect persists at least 4 hours after application of the glyceryl 1,3 distearate (see example 4).

An ex vivo assay allows also demonstrating that applying glyceryl 1,3 distearate on the skin makes it possible to limit the increased cutaneous penetration of a polluting agent such as benzo[a]pyrene due to heat.

An object of this invention thus relates to a topical cosmetic or dermatological composition comprising at least one 1,3 diglyceride having the general formula (I), in which the radicals R$_1$ and R$_2$ represent, independently of one another, a C13 to C40 saturated and linear alkyl radical; and further comprising at least one cosmetic or dermatological excipient for a topical application on the skin.

The 1,3 diglycerides having the general formula (I) hereinabove can be prepared in particular as described in the article of Liu et al. [9]. They are used in the compositions according to the invention, as an active principle, and more particularly as a stabilising agent of the intercorneocytory spaces.

The term "intercorneocytory spaces" means the spaces containing a lipid phase which are located between the corneocytes of the cornea layer (also called stratum corneum—SC in abstract) which forms the skin barrier.

In the framework of this patent application, the term "stabilising agent of the intercorneocytory spaces" will be used more particularly to designate an agent that limits the destabilisation of the intercorneocytory spaces, in particular under the action of environmental factors, and which therefore has a barrier effect by opposing the penetration of exogenous substances, such as chemical or microbial agents that can be irritating and/or allergenic; or polluting agents that can generate an oxidative stress, in a skin in particular exposed to environmental factors.

This effect of stabilisation/destabilisation of the intercorneocytory spaces can among others be evaluated according to the protocol of the example 2.

Concerning the penetration of exogenous substances, an ex vivo assay (see example 6) allows evidencing the fact that the bioavailability of benzo[a]pyrene is highly influenced by the skin temperature: it doubles when the skin temperature passes from 32° C. to 42° C. (increasing from 2.95 to 6.95% of the dose applied to the skin).

This illustrates the need to strengthen the skin barrier by stabilizing the intercorneocytory spaces to limit the penetration of exogenous substances, in particular when environmental conditions lead to an increase in outside temperature notably greater than or equal to about 42° C.

The ex vivo assay on the bioavailability of benzo[a]pyrene after application of a 1,3 diglyceride of formula I on the tested skin also confirms that the 1,3 diglyceride compounds as defined previously allow this stabilisation and thus the skin protection.

Indeed, after application of a 1,3 diglyceride of formula I, and more particularly glyceryl 1,3 distearate at the dose of 3% or 15%, on a skin maintained in an atmosphere at 42° C., a significant decrease in the penetration of benzo[a]pyrene compared to the basal state and the vehicle was observed.

The term "environmental factors" means, in the terms of this invention, the external conditions such as heat or cold, preferably heat, that induce a variation in the skin temperature that can destabilise the intercorneocytory spaces. In a preferred embodiment, heat, such as that of a summer period or due to an exposure to the sun, can induce an elevation in the skin temperature, notably above about 35° C., in particular above about 40° C., and cause a fluidification of the lipids of the intercorneocytory spaces in terms of this invention.

The impact of the external temperature on the organisation of the intercorneocytory spaces of the stratum corneum can among others be evaluated according to the model of example 1 (analysis via infrared spectroscopy of the variation in the wave number of the $\nu CH_2$ vibration).

In this respect, as has already been mentioned, it has been shown that a simple exposure for an average of 3 hours in conditions of average outdoor sunshine (outside temperature of 26.6° C.) was sufficient to induce an increase of 4.7° C. in the skin temperature (initially at 31.7° C.) [6] and that the latter can exceed 40° C. after only 20 minutes of exposure to the sun at solar noon in the summer [7].

Such an elevation in the skin temperature then causes a fluidification of the lipids of the intercorneocytory spaces, which develops into a state of the liquid crystal type giving rise to a substantial increase in transepidermal water loss [4].

In a particular embodiment of the invention, the radicals R$_1$ and R$_2$ are identical and represent a C13 to C40 saturated and linear alkyl radical.

According to another embodiment of the invention, the radicals R$_1$ and R$_2$ represent, independently of one another, a C15 to C23, in particular a C15 to C19, saturated and linear alkyl radical. The radicals R$_1$ and R$_2$ can also be identical and represent a C15 to C23, in particular a C15 to C19, saturated and linear alkyl radical.

The radicals R$_1$ and R$_2$, identical or different, preferably identical, represent in particular the hydrocarbon chain of palmitic, stearic or arachidic acid, namely a pentadecyle, heptadecyle or nonadecyle radical.

The diglyceride 1,3 according to the invention will be more particularly glyceryl 1,3 dipalmitate, glyceryl 1,3 distearate or a mixture thereof.

The 1,3 diglycerides having the formula (I) according to the invention represent preferably from 0.5 to 10%, more particularly from 1 to 5%, and even more particularly from 3 to 5% by weight of the total weight of the composition.

According to another embodiment, the 1,3 diglycerides having the formula (I) according to the invention represent from 5 to 10% by weight of the total weight of the composition.

The compositions according to this invention can also contain a 1,2 diglyceride. Indeed, the 1,3 diglycerides used generally contain small residual quantities of 1,2 diglyceride. However, the quantity of 1,2 diglyceride in the compositions according to the invention will not exceed advantageously 10% by weight, in particular 5% by weight, of the total weight of the 1,3 and 1,2 diglycerides.

The topical compositions according to the invention are intended to be applied on the skin. These compositions can be more or less fluid and have the aspect of a cream, a lotion, a milk, a serum, an ointment, a gel or a foam. They can also have the form of a solid, such as a stick or be applied on the skin in the form of an aerosol. These compositions can in particular have the form of an oily solution; of an oil-in-water, water-in-oil emulsion, or multiple emulsions.

The 1,3 diglycerides having the formula (I) according to the invention will preferably be introduced into the compositions in dispersed form.

By "dispersed form" is meant in the present invention that the 1,3 diglyceride having the formula (I) according to the invention is in the form of solid particles which are dispersed in a dispersing phase.

Thus, the compositions according to the invention will comprise advantageously at least one 1,3 diglyceride having the formula (I) according to the invention in a dispersed form, i.e. present in the composition in the form of dispersed solid particles.

According to a preferred embodiment, the average diameter of the solid particles of 1,3-diglyceride of formula (I) according to the invention is greater than 100 nm and less than 50 μm. A measure of the particle size distribution by laser diffraction allows obtaining such a value.

In a particular embodiment, the 1,3-diglycerides of formula (I) according to the invention will be dispersed in a fatty phase, for example a silicone and preferably a non-volatile silicone, an ester, a mineral oil or a vegetable oil, or a mixture thereof. Among the silicones, dimethicone (non-volatile) can be mentioned.

The composition according to the invention provides a protection of the skin barrier, that remains comfortable all throughout the day. It can in particular be applied to sensitive, fragile and/or reactive skin, and in particular to the skin of a baby.

This invention also has for object a composition according to the invention described hereinabove for use in the protection of the skin, including facial skin, body skin and scalp.

This invention also relates to the use of a composition described hereinabove in order to protect the skin, including facial skin, body skin and scalp.

This invention also relates to a method for protecting the skin, including facial skin, body skin and scalp, comprising the administration to a person in need thereof of an effective quantity of a composition described hereinabove.

This invention also has for object a composition according to the invention described hereinabove for use in countering the weakening of the skin barrier.

This invention also relates to the use of a composition described hereinabove in order to counter the weakening of the skin barrier.

This invention also relates to a method for countering the weakening of the skin barrier comprising the administration to a person in need thereof of an effective quantity of a composition described hereinabove.

This invention also has for object the compositions described hereinabove for use for preventing or reducing the penetration of exogenous molecules into the skin following a weakening of the skin barrier.

This invention also relates to the use of a composition described hereinabove for preventing or reducing the penetration of exogenous molecules into the skin following a weakening of the skin barrier.

This invention also relates to a method for preventing or for reducing the penetration of exogenous molecules following a weakening of the skin barrier comprising the administration to a person in need thereof of an effective quantity of a composition described hereinabove.

The weakening of the skin barrier can be induced in particular under the effect of environmental factors such as the cold or heat, and more particularly heat, in particular in case of exposure to the sun.

This weakening results in particular in a destabilisation of the intercorneocytory spaces, a destabilisation which can among others be evaluated according to the protocol of the example 1.

The exogenous molecules can be in particular irritant substances (hygiene products, solvents, etc.) or allergenic substances (perfumes, house dust, microbial agents, etc.). In particular, the exogenous molecules are lipophilic.

This invention also has for object a 1,3 diglyceride having the general formula (I) hereinbelow:

(I)

in which the radicals $R_1$ and $R_2$ represent, independently of one another, a C13 to C40 saturated and linear alkyl radical, for use in the protection of the skin, including facial skin, body skin and scalp.

This invention also relates to the use of a 1,3 diglyceride having the general formula (I) hereinbelow:

(I)

in which the radicals $R_1$ and $R_2$ represent, independently of one another, a C13 to C40 saturated and linear alkyl radical, for the manufacture of a topical cosmetic or dermatological composition intended to protect the skin, including facial skin, body skin and scalp.

This invention also relates to the use of a 1,3 diglyceride having the general formula (I) hereinbelow:

in which the radicals $R_1$ and $R_2$ represent, independently of one another, a C13 to C40 saturated and linear alkyl radical, in order to protect the skin, including facial skin, body skin and scalp.

This invention also relates to a method for protecting the skin, including facial skin, body skin and scalp, comprising the administration to a person in need thereof of an effective quantity of a 1,3 diglyceride having the general formula (I) hereinbelow:

in which the radicals $R_1$ and $R_2$ represent, independently of one another, a C13 to C40 saturated and linear alkyl radical.

This invention also has for object a 1,3 diglyceride having the general formula (I) hereinbelow:

in which the radicals $R_1$ and $R_2$ represent, independently of one another, a C13 to C40 saturated and linear alkyl radical, for use to counter the weakening of the skin barrier.

This invention also relates to the use of a 1,3 diglyceride having the general formula (I) hereinbelow:

in which the radicals $R_1$ and $R_2$ represent, independently of one another, a C13 to C40 saturated and linear alkyl radical, for the manufacture of a topical cosmetic or dermatological composition intended to counter the weakening of the skin barrier.

This invention also relates to the use of a 1,3 diglyceride having the general formula (I) hereinbelow:

in which the radicals $R_1$ and $R_2$ represent, independently of one another, a C13 to C40 saturated and linear alkyl radical, in order to counter the weakening of the skin barrier.

This invention also relates to a method for countering the weakening of the skin barrier comprising the administration to a person in need thereof of an effective quantity of a 1,3 diglyceride having the general formula (I) hereinbelow:

in which the radicals $R_1$ and $R_2$ represent, independently of one another, a C13 to C40 saturated and linear alkyl radical.

This invention also has for object a 1,3 diglyceride having the general formula (I) hereinbelow:

in which the radicals $R_1$ and $R_2$ represent, independently of one another, a C13 to C40 saturated and linear alkyl radical, for its topical use in preventing or reducing the penetration of exogenous molecules following a weakening of the skin barrier.

This invention also relates to the use of a 1,3 diglyceride having the general formula (I) hereinbelow:

in which the radicals $R_1$ and $R_2$ represent, independently of one another, a C13 to C40 saturated and linear alkyl radical, for the manufacture of a topical cosmetic or dermatological composition intended to prevent or reduce the penetration of exogenous molecules following a weakening of the skin barrier.

This invention also relates to the use of a 1,3 diglyceride having the general formula (I) hereinbelow:

in which the radicals $R_1$ and $R_2$ represent, independently of one another, a C13 to C40 saturated and linear alkyl radical, for preventing or reducing the penetration of exogenous molecules following a weakening of the skin barrier. In particular, the exogenous molecules are lipophilic.

This invention also relates to a method for preventing or for reducing the penetration of exogenous molecules following a weakening of the skin barrier comprising the administration to a person in need thereof of an effective quantity of a 1,3 diglyceride having the general formula (I) hereinbelow:

in which the radicals $R_1$ and $R_2$ represent, independently of one another, a C13 to C40 saturated and linear alkyl radical.

The weakening of the skin barrier can be induced in particular under the effect of environmental factors such as the cold or heat, and more particularly heat, in particular in case of exposure to the sun.

This weakening results in particular in a destabilisation of the intercorneocytory spaces, a destabilisation which can among others be evaluated according to the protocol of the example 1.

The exogenous molecules can be in particular irritant substances (hygiene products, solvents, etc.) or allergenic substances (perfumes, house dust, microbial agents, etc.).

In a particular embodiment of the invention, the radicals $R_1$ and $R_2$ are identical and represent a C13 to C40 saturated and linear alkyl radical.

According to another embodiment of the invention, the radicals $R_1$ and $R_2$ represent, independently of one another, a C15 to C23, in particular a C15 to C19, saturated and linear alkyl radical. The radicals $R_1$ and $R_2$ can also be identical and represent a C15 to C23, in particular a C15 to C19, saturated and linear alkyl radical.

The radicals $R_1$ and $R_2$, identical or different, more preferably identical, represent in particular the hydrocarbon chain of palmitic, stearic or arachidic acid, namely a pentadecyle, heptadecyle or nonadecyle radical.

The 1,3 diglyceride according to the invention shall be more particularly glyceryl 1,3 dipalmitate, glyceryl 1,3 distearate or a mixture thereof.

The following examples and figures show the invention.

EXAMPLES

Example 1: Modification of the Organisation of the Intercorneocytory Spaces Under the Influence of Heat The study was carried out on lipids extracted from the stratum corneum of the forearm in order to have a model as close as possible to reality. We have used infrared spectroscopy (ATR-FTIR), to examine the variation, in function of temperature, of fundamental $vCH_2$ vibration bands of aliphatic chains.

Figure 1:
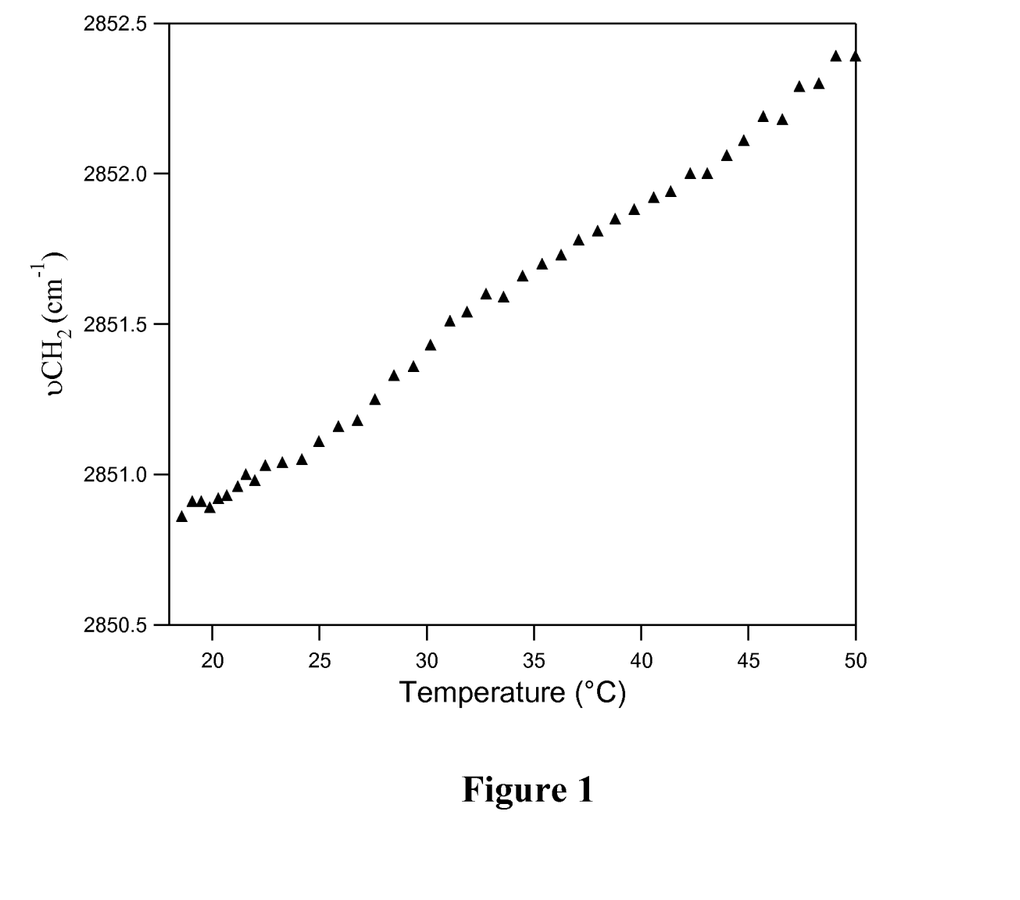
FIG. 1 shows the wave number of the $vCH_2$ vibration of the aliphatic chains of the intercorneocytory lipids in function of temperature.

The variation in the wave number of the $vCH_2$ vibration in function of temperature between 18 and 50° C. is reported in FIG. 1.

It is noted that at low temperatures the value of the $vCH_2$ stretching vibration of the mixture of pure lipids is located at 2850.7 $cm^{-1}$, which is characteristic of an Orthorhombic/Hexagonal phase, and that the latter changes at higher temperatures to higher wave numbers, in order to reach 2852.4 $cm^{-1}$, characteristic of a Liquid phase.

The increase in the wave number observed indeed reveals the change in state and the fluidification of the intercorneocytory lipids under the effect of the temperature.

Figure 2:
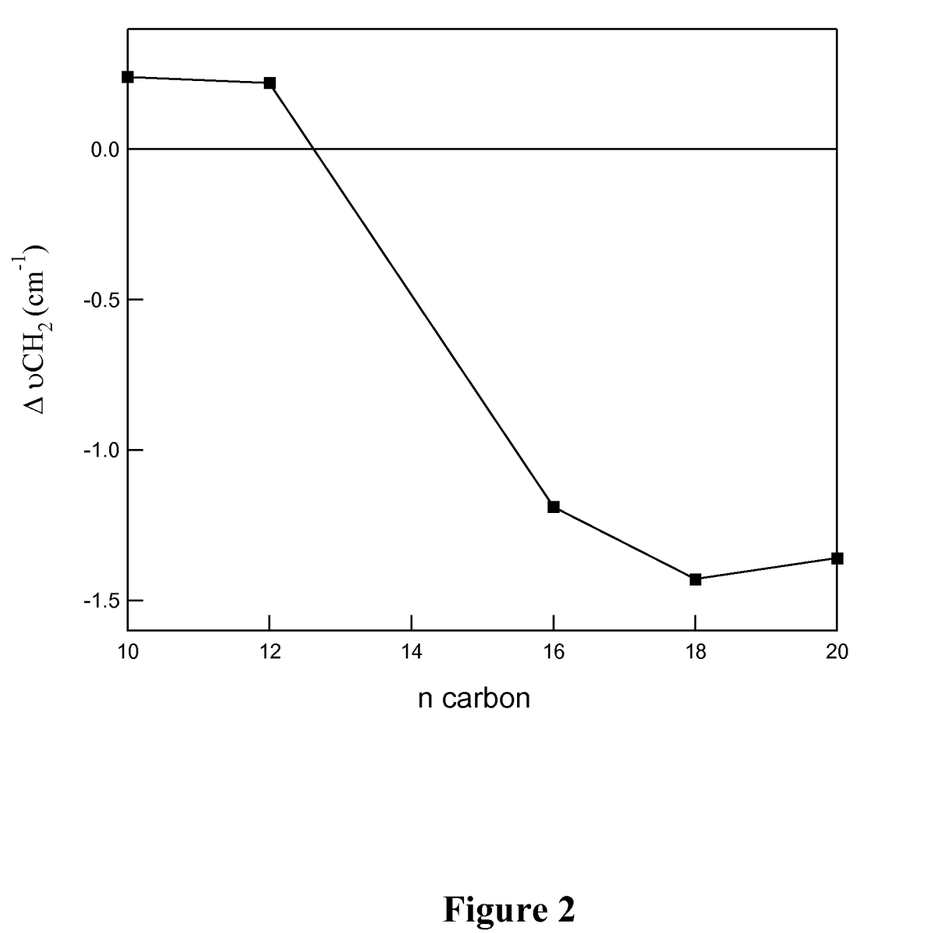
FIG. 2 shows the variation in the wave number of the $vCH_2$ vibration of the aliphatic chains of the intercorneocytory lipids, between the situations with or without 1,3 diglyceride, according to the length of the chain of the 1,3 diglyceride.

Example 2: Revealing of the Stabilising Effect of 1,3 Diglycerides and of the Effect of their Chain Length on the Organisation of the Intercorneocytory Lipids The tests were carried out in similar experimental conditions using lipids extracts from the forearm wherein a standardized quantity of diglyceride is added (3 µg of diglyceride for 30 µg of sample). FIG. 2 shows the effect of the chain length of the 1,3 diglyceride on the $vCH_2$ parameter, with the measurements taken at 40° C.

These results make it possible to reveal the influence of the length of the aliphatic chains of glycerides. At temperatures close to living organisms, 1,3-dicaprin (C10) as well as 1,3-dilauroylglycerol (C12) have no influence on the organisation of the intercorneocytory lipids. As it appears when examining FIG. 2, starting from a C14 chain length, a significant stabilising effect appears and starting from a C16 chain length, it can be seen that the stretching frequency of the $CH_2$ is maintained towards the low numbers comparatively to the extract devoid of diglyceride. Furthermore, these results indeed reveal an increase in the stabilising power with the length of the alkyl chain of the diglycerides with respect to the fluidification of the skin lipids under the effect of heat.

Example 3: 1,3 Diglyceride/1,2 Diglyceride Comparison

The test of the example 2 was reproduced with 1,2-distearoyl-rac-glycerol (1,2 diglyceride) and compared to the test carried out with glyceryl 1,3-distearate (1,3 diglyceride). The results obtained are shown in table 1 hereinbelow.

TABLE 1 variation in the wave number of the $vCH_2$ vibration of the aliphatic chains of the intercorneocytory lipids, between the situations with or without 1,3 diglyceride, for a 1,3 diglyceride and a 1,2 diglyceride.

| Glyceride | $\Delta vCH2$ (cm$^{-1}$) |
|---|---|
| glyceryl 1,3-distearate | −1.43 |
| 1,2-distearoyl-rac-glycerol | −0.65 |

These results clearly show the superior effect of 1,3 diglycerides on the stabilisation of intercorneocytory spaces.

Example 4: Revealing of the Stabilising Effect of the Organisation of the Intercorneocytory Spaces after Application of Glyceryl 1,3-Distearate in Clinical Conditions In Vivo This study was carried out on health volunteers. The collection of infrared data was done through the intermediary of the ATR-FTIR sensor on the inner face of the forearm on a zone of 10 cm$^2$.

A treated zone (with application in vivo of glyceryl 1,3 distearate) and a control zone (without application of glyceryl 1,3 distearate) were determined.

Two concentrations in glyceryl 1,3-distearate were evaluated (table 2: 0.5 mg/cm$^2$ and table 3: 0.15 mg/cm$^2$).

At T0: the skin is first heated to between 30 and 45° C.

Then after application in vivo of glyceryl 1,3-distearate on the treated zone, an evaluation is made of the variation in the wave number associated with the $vCH_2$ vibration comparatively to the reference measurement without product applied (control zone) at different times after T0: T 30 minutes, T 1 h30 minutes and T 4 hours.

The data obtained is gathered together in tables 2 and 3 and allows several observations to be made.

TABLE 2 applied quantity of glyceryl 1,3-distearate = 0.5 mg/cm$^2$

| $\Delta vCH2$ 0.5 mg/cm$^2$ | 30 min | 1 h 30 | 4 h |
|---|---|---|---|
| Subject 1 | −2.56 | −2.65 | −2.6 |
| Subject 2 | −3.02 | −2.62 | −2.29 |
| Subject 3 | −2.71 | −2.6 | −2.18 |
| Average (cm$^{-1}$) | −2.46 | −2.41 | −2.17 |

TABLE 3 applied quantity of glyceryl 1,3-distearate = 0.15 mg/cm$^2$

| $\Delta vCH2$ 0.5 mg/cm$^2$ | 30 min | 1 h 30 | 4 h |
|---|---|---|---|
| Subject 4 | −1.87 | −1.91 | −1.64 |
| Subject 5 | −2.16 | −2.25 | −2.15 |
| Average (cm$^{-1}$) | −2.02 | −2.08 | −1.89 |

Tables 2 and 3: express the variation of the wave number associated with the $vCH_2$ vibration of the aliphatic chains of the intercorneocytory lipids at 40° C. in the presence of glyceryl 1,3-distearate comparatively to the reference measurement without glyceryl 1,3-distearate.

Firstly, it is shown without ambiguity that the glyceryl 1,3-distearate in normal conditions of use makes it possible to stabilise the organisation of the intercorneocytory spaces of the skin heated between 30 and 45° C.

Secondly, it is shown that this stabilising effect visible as soon as the diglyceride is applied lasts for at least 4 hours.

Example 5: Examples of Compositions According to the Invention

Composition 1: O/W Formula

| Components | % by weight |
|---|---|
| Glyceryl 1,3 dipalmitate | 1-5 |
| Glycerine | 10.0 |
| Na$_2$EDTA | 0.1 |
| Xanthan gum | 0.3 |
| C12-C15 alkyl benzoate | 10.0 |
| Octyl palmitate | 5.0 |
| Preservatives | qs |
| Stearic alcohol | 2.5 |
| Glycerol monostearate | 2.5 |
| Potassium cetyl phosphate | 1.8 |
| Demineralised water | QSP 100 |

Composition 2: W/O Formula

| Components | % by weight |
|---|---|
| Glyceryl 1,3 distearate | 1-5 |
| Glycerine | 4.0 |
| Na$_2$EDTA | 0.1 |
| MgSO$_4$ | 1.0 |
| Xanthan gum | 0.1 |
| C12-C15 alkyl benzoate | 12.5 |
| Isohexadecane | 3.5 |
| Cyclomethicone | 3.0 |
| Preservatives | qs |
| Sorbitane and polyglycerol esters | 4.0 |
| Myreth-3 myristate | 2.0 |
| Demineralised water | Qsp 100 |

Composition 3: Creamy Gel

| Components | % by weight |
|---|---|
| Glyceryl 1,3 dipalmitate | 1-5 |
| Dimethicone | 5.0 |
| C8-C18 alkyl ester | 5.0 |
| Polyethylene glycol glyceryl cocoate (Cetiol ® HE) | 2.5 |
| Polyacrylate 13 & Polyisobutene & Polysorbate 20 (Sepiplus ™ 400) | 3.0 |
| Xanthan gum | 0.1 |
| Propylene glycol | 3.0 |
| Na$_2$EDTA | 0.2 |
| Preservatives | qs |
| Demineralised water | Qsp 100 |

Composition 4: Cream

| Components | % by weight |
| --- | --- |
| Glyceryl 1,3 distearate | 3-10 |
| Dimethicone | 5.0 |
| Glyceryl stearate/PEG-100 stearate (Simulsol ™ 165) | 5.0 |
| Behenic alcohol | 1.3 |
| Octyldodecanol | 10.0 |
| C8-C18 alkyl ester | 5.0 |
| Polyacrylate 13 & Polyisobutene & Polysorbate 20 (Sepiplus ™ 400) | 2.0 |
| Propylene glycol | 3.0 |
| Na$_2$EDTA | 0.2 |
| Preservatives | qs |
| Demineralised water | Qsp 100 |

Example 6: Evaluation of the Impact of 1,3 Diglycerides on the Benzo[a]Pyrene Skin Penetration In order to evaluate the impact of 1,3-diglycerides on the organization of stratum corneum lipids and barrier function, in vitro, skin penetration studies of a known pollutant (benzo[a]pyrene (B(a)P) has been developed and performed. On the same donors, FTIR (Fourier transform infrared) measurement and B(a)P skin penetration were assessed to link lipid organization and the "outside-in" skin barrier function modulations, when the skin is heated up to 42° C.

Firstly, it has been demonstrated that an increase of temperature from 32° C. to 42° C. at the surface of the skin modifies the lipid organization and alters the "outside-in" skin barrier function as evidenced by an increase of the skin penetration of B(a)P.

Secondly, the impact of pre-treatment with 3% and 15% of glyceryl 1,3 distearate formulated in dimethicone on the modification of the SC (stratum corneum) lipid organization and B(a)P skin penetration provoked by the temperature elevation has been evaluated.

Material and Methods

Compounds

Test Items

| TEST ITEM NAME | SUPPLIER | MW | STOCK SOLUTION |
| --- | --- | --- | --- |
| Glyceryl 1,3 distearate | Sigma Aldrich | 625.02 | 3% and 15% in dimethicone |
| Benzo[a]pyrene | Sigma Aldrich | 252.31 | In acetone at 0.5% |
| C$^{14}$-Benzo[a]pyrene | Isobio | 252.31 | In acetone at 0.5% |

Solubility

The solubility of B(a)P is well documented in the literature. Due to its physicochemical properties, B(a)P has a very poor solubility in water. The software Episuite predict a solubility of 13.3 µg/L and experimental data confirmed this result at 25° C. [11]. In the present study, the percentage of B(a)P found in the receptor fluid reach 0.13% of the applied dose in the worst case, corresponding to 12.51 µg/L. Based on these data, we have added 4% of bovine serum albumin (BSA) to increase the solubility of B(a)P and avoid to damage the skin. Surfactants and ethanol were prohibited in order to avoid modification of skin barrier function.

Guidelines

The study was performed according to:
OECD Guidelines for the testing of chemicals: guideline 428, skin absorption: in vitro method (13 Apr. 2004);
SCCS Guidelines, basic criteria for the in-vitro assessment of dermal absorption of cosmetics ingredients, updated March 2006.

Experimental Design

Set of the temperatures:
FTIR measurement:
The skin samples were heated at the rate of 1° C./min, and spectra were collected between 28° C. and 43° C.

| Kinetic of heating | 1° C./min |
| --- | --- |
| Minimal temperature tested | 28° C. |
| Maximal temperature tested | 43° C. |

Skin Delivery Experiment

For the skin delivery study, two temperatures were set. The classical temperature at the surface of the skin for skin delivery studies is 32° C. This temperature corresponds to the temperature at the surface of the skin in vivo. Previous studies performed by the Biophysic and Imaging Unit on in vitro lipids with FTIR shown that at 40° C. the disorganization of the lipids starts to be visible. Based on these results, a temperature of 42° C. has been chosen to be able to observe the disorganisation of the lipids during the skin delivery experiment.

| | |
| --- | --- |
| 32° C. | Without pre-treatment |
| | Dimethicone |
| | 3% Glyceryl 1,3 distearate |
| | 15% Glyceryl 1,3 distearate |
| 42° C. | Without pre-treatment |
| | Dimethicone |
| | 3% Glyceryl 1,3 distearate |
| | 15% Glyceryl 1,3 distearate |

Skin Delivery Experiment

| Pre-treatment | Glyceryl 1,3 distearate at 3% and 15% in dimethicone |
| --- | --- |
| Time of pre-treatment | 30 min |
| Formulation | B(a)P in acetone |
| Theoretical B(a)P concentration in the formulation | 0.5% |
| Cell system | Franz diffusion cell (1.2 cm$^2$) |
| Skin | Human skin |
| Formulation applied per cell (mg) | 10 µl/cm$^2$ |
| Skin temperature | 32° C. ± 1° C. |
| Skin integrity | TEWL ≤ 13 g/m$^2$/h |
| Theoretical amount of B(a)P applied on skin | 52 µg/cm$^2$ |
| Thickness of the skin | 400 ± 50 µm |

-continued

| Pre-treatment | Glyceryl 1,3 distearate at 3% and 15% in dimethicone |
|---|---|
| Number of cell per donor | 1 |
| Number of donor per condition | 8 |
| Total cells | 64 |
| Temperature of incubation | 32° C. and 42° C. |
| Washing of the formulation | 24 hours after application |
| Surface | 2 times with water |
| | 2 times with acetonitrile (ACN) |
| | 2 times with ½ Whatman discs |
| Receptor fluid | NaCl 0.9% + BSA 4% |
| Sampling of receptor fluid | No |
| Separation of epidermis and dermis | No |
| Strips | 15 strips (D-Squame ®) |
| Solvent used | Acetonitrile |

The skin penetration study was carried out on 8 donors, the same donor was used for all the conditions:

| 32° C. | Without pre-treatment |
| | Dimethicone |
| | 3% Glyceryl 1,3 distearate |
| | 15% Glyceryl 1,3 distearate |
| 42° C. | Without pre-treatment |
| | Dimethicone |
| | 3% Glyceryl 1,3 distearate |
| | 15% Glyceryl 1,3 distearate |

Lipids organization—FTIR measurement:
After 30 min of pre-treatment, FTIR measurements were performed to evaluate the molecular organization of the lipid matrix in the stratum corneum. The procedure is based on the study of the position of the $CH_2$ symmetric stretching band, around 2850 $cm^{-1}$, depending on the temperature: the skin samples were heated at the rate of 1° C./min and spectra were collected between 28° C. and 43° C. with and without pre-treatment. The position of the $CH_2$ symmetric stretching band is characteristic of the lipid organization and can be related to the barrier function.

Read-Out Parameters

FTIR measurement of skin explant (position of $CH_2$ symmetric stretching band) depending on the temperature;
Skin penetration study
  Total recovery of B(a)P
  Compartmental repartition in percentage of B(a)P applied
  Compartmental repartition in $\mu g/cm^2$ Data Management The study was carried out on 8 donors, the same donor was used for all the conditions. B(a)P recovery should be comprised between 85% and 115% of the applied dose, in accordance with OECD 428 and SCCS guidelines.
Results of B(a)P were presented in Tables and Graphs expressed as:
  % of the applied dose at surface, stratum corneum, skin and receptor fluid;
  $\mu g/cm^2$ of B(a)P at surface, stratum corneum, skin and receptor fluid.

Results were presented with 2 decimals for the percentages and the quantities in $\mu g/cm^2$.
Formula used in this report:
  Standard error of the mean:
  sem=Sd/√n
  Bioavailability:
  Sum of the quantities found in the skin and receptor fluid.
The inter-group comparison was performed by a paired Student's t-test with Graph Pad Prism software. The statistical analysis can be interpreted if n>5.

Results

Lipids Organization—FTIR Measurement

Figure 3:
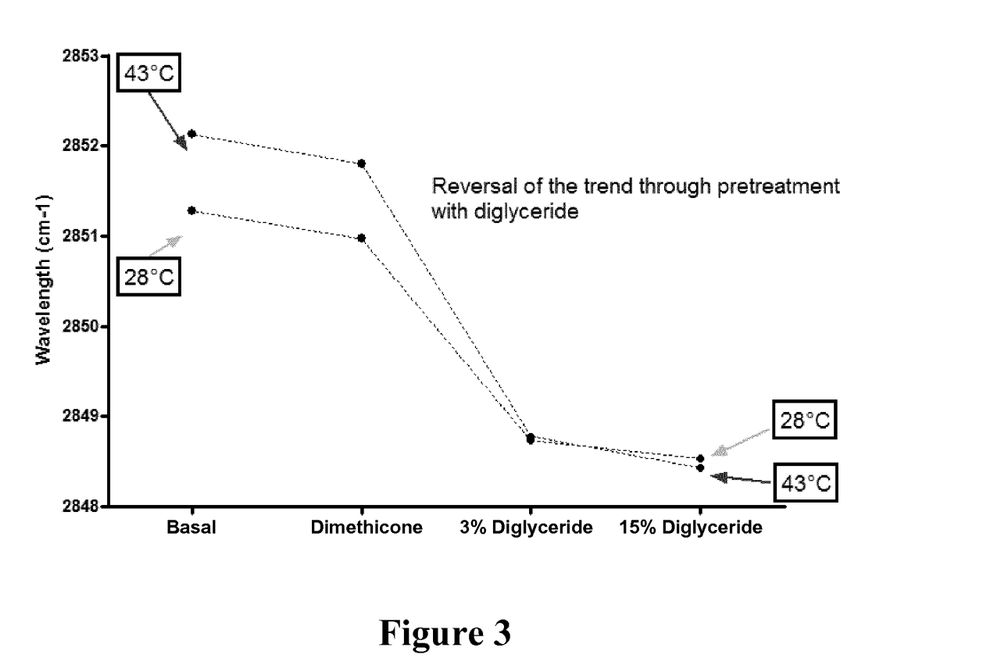
FIGS. 3 and 4 represent the $CH_2$ symmetric stretching band shift at 28° C. and 43° C. with or without pre-treatment of the skin.
Figure 4:
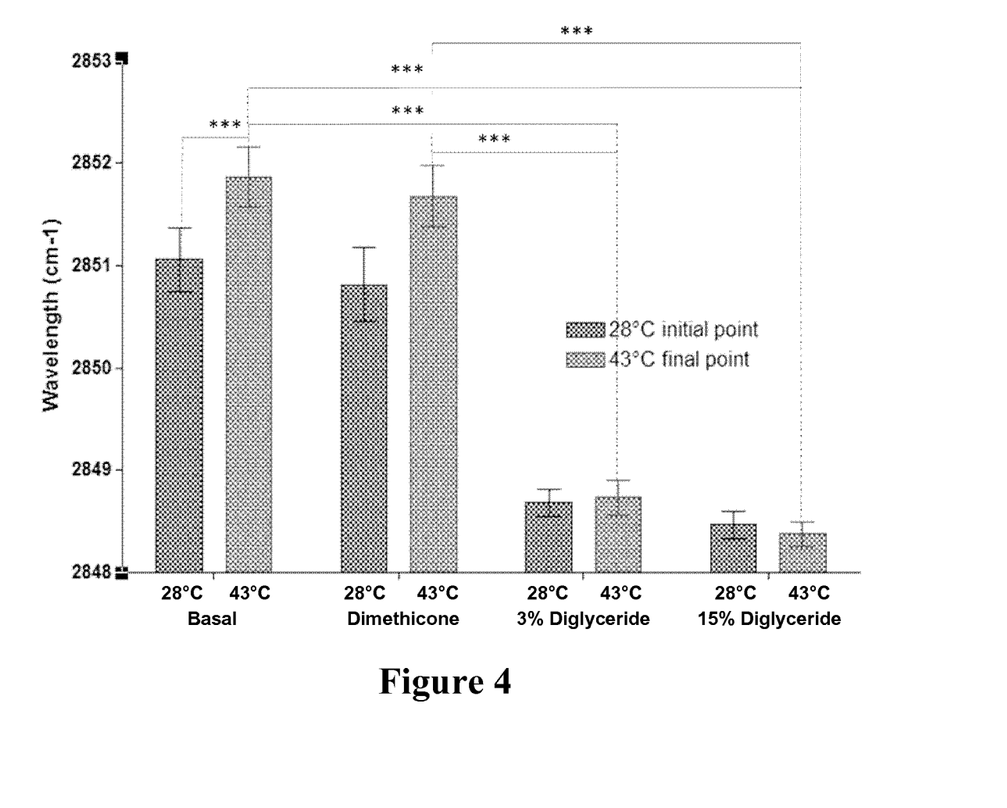

FTIR measurements were performed on human skin explants (8 donors) with or without pre-treatment. The skin samples were heated at the rate of 1° C./min, and spectra were collected between 28° C. and 43° C.
FIGS. 3 and 4 show the impact of the temperature on the $CH_2$ symmetric stretching band. Without pre-treatment, a significant difference on lipid organization can be seen when the skin is heated, with a shift of the $CH_2$ symmetric stretching band from 2851.2 $cm^{-1}$ at 28° C. to 2852.12 $cm^{-1}$ at 43° C. (T test, p value<0.05). The pre-treatment with 3% or 15% of glyceryl 1,3 distearate permits to decrease significantly (T tests, p value<0.05) the impact of the heating on the lipid organization. A shift of the $CH_2$ symmetric stretching band from 2852.12 $cm^{-1}$ (43° C. basal) to 2848.7 $cm^{-1}$ has been observed with 3% glyceryl 1,3 distearate as pre-treatment at 43° C. The pre-treatment with glyceryl 1,3 distearate decreases the shift of the $CH_2$ symmetric stretching band induced by the heating of the skin: the shift is only 0.05 $cm^{-1}$ after pre-treatment with 3% of glyceryl 1,3 distearate and 0.81 $cm^{-1}$ without pre-treatment.

Skin Penetration Study

Figure 5:
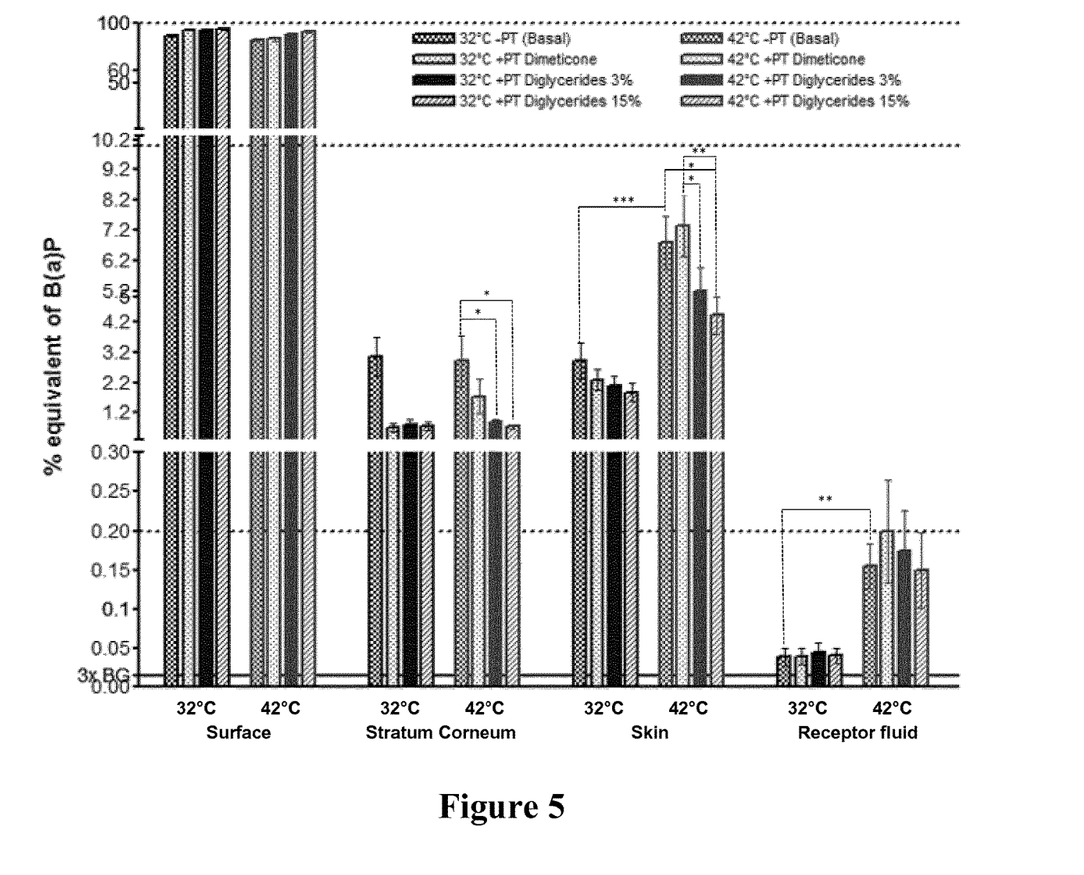
FIG. 5 represents the percentage of B(a)P recovered in the different compartments of the Franz diffusion cell after 24 h (Mean±SEM; n=8).

Total recovery:
The total recovery for all the diffusion cells was in the acceptance criteria, ranging between 94.9% and 97.6% of the applied dose, and permits to validate the study.
Compartmental repartition in percentage of the applied dose:
The results obtained are presented in Table 4 below and on FIG. 5.

TABLE 4

Summary results in percentage of the applied dose (Mean ± SEM; n = 8)

| | Without pretreatment | | Dimethicone | | 3% Diglyceride | | 15% Diglyceride | |
|---|---|---|---|---|---|---|---|---|
| | Mean | SEM | Mean | SEM | Mean | SEM | Mean | SEM |
| | 32° C. | | | | | | | |
| Surface | 89.38 | 1.49 | 94.42 | 0.70 | 94.66 | 0.47 | 94.99 | 0.47 |
| Stratum corneum | 3.05 | 0.63 | 0.72 | 0.12 | 0.82 | 0.16 | 0.77 | 0.15 |
| Skin | 2.91 | 0.58 | 2.28 | 0.34 | 2.09 | 0.32 | 1.87 | 0.30 |
| Receptor fluid | 0.04 | 0.01 | 0.04 | 0.01 | 0.05 | 0.01 | 0.04 | 0.01 |
| Bioavailability | 2.95 | 1.64 | 2.32 | 0.95 | 2.14 | 0.91 | 1.91 | 0.84 |
| Mass balance | 95.37 | 1.19 | 97.45 | 0.74 | 97.62 | 0.57 | 97.67 | 0.58 |
| | 42° C. | | | | | | | |
| Surface | 86.55 | 1.28 | 86.80 | 2.09 | 90.39 | 1.21 | 92.68 | 0.68 |
| Stratum corneum | 2.90 | 0.83 | 1.74 | 0.56 | 0.90 | 0.11 | 0.75 | 0.07 |
| Skin | 6.79 | 0.88 | 7.37 | 1.01 | 5.18 | 0.77 | 4.40 | 0.60 |

TABLE 4-continued

Summary results in percentage of the applied dose (Mean ± SEM; n = 8)

|  | Without pretreatment | | Dimethicone | | 3% Diglyceride | | 15% Diglyceride | |
| --- | --- | --- | --- | --- | --- | --- | --- | --- |
|  | Mean | SEM | Mean | SEM | Mean | SEM | Mean | SEM |
| Receptor fluid | 0.15 | 0.03 | 0.20 | 0.07 | 0.17 | 0.05 | 0.15 | 0.05 |
| Bioavailability | 6.95 | 2.45 | 7.57 | 2.81 | 5.35 | 2.15 | 4.55 | 1.71 |
| Mass balance | 96.40 | 0.59 | 96.11 | 1.44 | 96.64 | 0.90 | 97.99 | 0.57 |

The majority of the applied dose of B(a)P was recovered at the surface (up to 94.5% of the applied dose).

B(a)P bioavailability (skin+receptor fluid) is low at 32° C., i.e. up to 2.95% of the applied dose. B(a)P bioavailability increases significantly and reaches 6.95% of the applied dose when the skin is heated at 42° C. (T test, p value<0.05). The pre-treatment with the vehicle alone (dimethicone) does not modify significantly the bioavailability of B(a)P whatever the temperature of the skin (T test, p value<0.05).

After pre-treatment with glyceride 1,3 distearate as diglyceride at 3% or 15%, a significant decrease of the bioavailability of B(a)P is observed at 43° C. Indeed, 7.57% of the applied dose is bioavailable with the vehicle (dimethicone) and decreases to 5.35% and 4.35% of the applied dose after pre-treatment with 3% and 15% of glyceride 1,3 distearate, respectively.

At 42° C., the percentage of B(a)P found in the stratum corneum decreases after application of glyceride 1,3 distearate. For compounds with physicochemical properties as B(a)P (lipophilic compounds), stratum corneum, which is a lipophilic compartment, acts as a reservoir. Decreasing the percentage of B(a)P recovered in the stratum corneum thus prevents the diffusion of this compound in the deeper layers of the skin even if the skin is not heated.

The results obtained for the skin penetration of B(a)P correlate well with the results obtained from the FTIR measurement.

CONCLUSION

The results obtained for the skin penetration of B(a)P after 24 h skin application correlate well with the results obtained from the FTIR measurements. These data showed that the modification of the organisation of the lipids around 42° C. induces a weaker barrier function and increases the bioavailability of compounds like outdoor pollutants such as B(a)P. This shows that the use of 1,3-diglycerides improves significantly the barrier function; both pre-treatments with 3% and 15% of glyceride 1,3 distearate formulated in dimethicone have been evaluated. The pre-treatment with glyceride 1,3 distearate permits to stabilize the lipids organization (FTIR measurement) and improves the "outside-in" barrier function as demonstrated by the B(a)P skin penetration study. Even with 3% of glyceride 1,3 distearate as pretreatment, a significant improvement of the barrier function and lipid stabilization is observed.

BIBLIOGRAPHIC REFERENCES

[1] Fabienne Berthaud, Mila Boncheva. Correlation between the properties of the lipid matrix and the degrees of integrity and cohesion in healthy human stratum corneum. *Exp Dermatol*, 20(3):255-262, March 2011.

[2] Mila Boncheva, Fabienne Damien, Valéry Normand. Molecular organization of the lipid matrix in intact stratum corneum using atr-ftir spectroscopy. *Biochim Biophys Acta*, 1778(5):1344-1355, May 2008.

[3] Fabienne Damien, Mila Boncheva. The extent of orthorhombic lipid phases in the stratum corneum determines the barrier efficiency of human skin in vivo. *J Invest Dermatol*, 130(2):611-614, February 2010.

[4] Daniël Groen, Dana S. Poole, Gert S. Goons, Joke A. Bouwstra. Is an orthorhombic lateral packing and a proper lamellar organization important for the skin barrier function? *Biochimica and Biophysica Acta (BBA)—Biomembranes*, 1808(6):1529-1537, 2011.

[5] Coderch L, López O, de la Maza A, Parra J L. Ceramides and skin function. Am J Clin Dermatol. 2003, 4(2):107-29.

[6] Cho S, Lee M J, Kim M S, Lee S, Kim Y K, Lee D H, Lee C W, Cho K H, Chung J H. Infrared plus visible light and heat from natural sunlight participate in the expression of MMPs and type Iprocollagen as well as infiltration of inflammatory cell in human skin in vivo. *Journal of Dermatological Science* (2008) 50, 123-133

[7] Jin Young Seo, Jin Ho Chung. Thermal aging: A new concept of skin aging. *Journal of Dermatological Science Supplement*, 2(1):S13-S22, 2006. Proceedings of the 5th Annual Meeting of the Japanese Photoaging Research Society.

[8] Scalia S, Mezzena M, Ramaccini D. Encapsulation of the UV filters ethylhexyl methoxycinnamate and butyl methoxydibenzoylmethane in lipid microparticles: effect on in vivo human skin permeation. *Skin Pharmacol Physiol*. 2011, 24(4):182-9.

[9] Ning Liu, Yong Wang, Qiangzhong Zhao, Qingli Zhang, Mouming Zhao. Fast synthesis of 1,3-DAG by Lecitase® Ultra-catalyzed esterification in solvent-free system. *Eur. J Lipid Sci. Technol*. 2011, 113, 973-979.

[10] KR 2013058299, WO 03/014073 A1, JP02115117 A, JP52061240A

[11] May W E et al. J. Chem. Ref. Data 1983, 28: 197-200

The invention claimed is:

1. A method for countering the weakening of skin barrier comprising the administration to a person in need thereof of an effective quantity of a topical, cosmetic or dermatological composition comprising a 1,3 diglyceride having the general formula (I):

wherein the radicals $R_1$ and $R_2$ represent, independently of one another, a C15 to C19 saturated and linear alkyl radical, and at least one cosmetic or dermatological excipient for a topical application on the skin, wherein the 1,3 diglyceride is present in the topical, cosmetic or dermatological composition in a quantity of between 0.5% and 10% by weight with respect to the total weight of the topical, cosmetic or dermatological composition, and wherein 1,2 diglyceride may be present in the topical, cosmetic or dermatological composition in a quantity that does not exceed 10% by weight of the total weight of the 1,3 and 1,2 diglycerides.

2. The method according to claim 1, wherein the skin barrier is weakened under the effect of environmental factors.

3. The method according to claim 2, wherein the environmental factor is the cold or heat.

4. The method according to claim 1, wherein $R_1$ and $R_2$ are identical.

5. The method according to claim 1, wherein the 1,3 diglyceride is glyceryl 1,3 dipalmitate, glyceryl 1,3 distearate or a mixture thereof.

6. The method according to claim 1, wherein the 1,3 diglyceride is present in the composition in the form of dispersed solid particles.

7. A method for countering the weakening of skin barrier and treating or preventing an irritation, an allergic reaction or an oxidative stress comprising the administration to a person in need thereof of an effective quantity of a topical, cosmetic or dermatological composition comprising:

a 1,3 diglyceride having the general formula (I):

(I)

wherein the radicals $R_1$ and $R_2$ represent, independently of one another, a C15 to C19 saturated and linear alkyl radical, and at least one cosmetic or dermatological excipient for a topical application on the skin, wherein the 1,3 diglyceride is present in the topical, cosmetic or dermatological composition in a quantity of between 0.5% and 10% by weight with respect to the total weight of the topical, cosmetic or dermatological composition, and wherein 1,2 diglyceride may be present in the topical, cosmetic or dermatological composition in a quantity that does not exceed 10% by weight of the total weight of the 1,3 and 1,2 diglycerides.

8. The method according to claim 7, wherein $R_1$ and $R_2$ are identical.

9. The method according to claim 7, wherein the 1,3 diglyceride is glyceryl 1,3 dipalmitate, glyceryl 1,3 distearate or a mixture thereof.

10. The method according to claim 7, wherein the 1,3 diglyceride is present in the composition in the form of dispersed solid particles.

* * * * *